US006844011B1

(12) United States Patent
Faustman

(10) Patent No.: US 6,844,011 B1
(45) Date of Patent: Jan. 18, 2005

(54) METHODS FOR INHIBITING REJECTION OF TRANSPLANTED TISSUE

(75) Inventor: Denise Faustman, Weston, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 08/925,627

(22) Filed: Sep. 9, 1997

Related U.S. Application Data

(63) Continuation of application No. 08/112,709, filed on Aug. 26, 1993, now Pat. No. 5,783,216, which is a division of application No. 07/671,517, filed on Mar. 19, 1991, now Pat. No. 5,283,058, which is a continuation-in-part of application No. 07/575,150, filed on Aug. 30, 1990, now abandoned.

(51) Int. Cl.$^7$ ............................................... A61K 35/14
(52) U.S. Cl. .................... 424/534; 424/570; 424/93.21; 424/178.1; 424/184.1; 435/2; 530/350
(58) Field of Search ...................... 530/350; 424/178.1, 424/184.1, 570, 534, 93.21; 514/2; 435/2

(56) References Cited

U.S. PATENT DOCUMENTS

| 5,284,931 A | 2/1994 | Springer et al. |
| 6,139,835 A | 10/2000 | Kucherlapati et al. |

FOREIGN PATENT DOCUMENTS

| JP | A S51-124094 | 10/1976 |
| WO | WO 90/03400 | 4/1990 |
| WO | WO 90/03812 | 4/1990 |

OTHER PUBLICATIONS

Stock et al., Journal of Surgical Research 46, 317–321 (1989).*
Faustman et al., PNAS USA 78, 5156 (1981).*
Adams et al., "Non–Tolerance and Autoantibodies to a Transgenic Self Antigen Expressed in Pancreatic β Cells," *Nature* 325:223–228 (1987).
Roitt, *Essential Immunology*, 4$^{th}$ Edition, Blackwell Scientific Publications, pp. 272–276 (1980).
Roitt, *Essential Immunology*, 5$^{th}$ Edition, Blackwell Scientific Publications, pp. 287–292, (1984).
Zijlstra et al., "β2–Microglobulin Deficient Mice Lack CD4$^-$8$^+$ Cytolytic T Cells," *Nature* 344:742–746 (1990).
Faustman et al., "Prolongation of murine islet allograft survival by pretreatment of Islets with antibody directed to Ia determinants," *Proc. Natl. Acad. Sci. USA* 78:5156–5159 (1981).
Koller et al., "Inactivating the β$_2$–microglobulin locus in mouse embryonic stem cells by homologous recombination," *Proc. Natl. Acad. Sci.USA* 86:8932–8935 (1989).

* cited by examiner

*Primary Examiner*—Laurie Scheiner
(74) *Attorney, Agent, or Firm*—Clark & Elbing LLP

(57) ABSTRACT

A method for inhibiting rejection by a recipient animal of a transplanted tissue, said method comprising modifying, eliminating, or masking an antigen which, when present on the surface of a cell of said tissue, is capable of causing a T-lymphocyte-mediated response in said animal, to inhibit antigen-mediated interaction between said cell and a T-lymphocyte of said animal without causing lysis of said cell.

7 Claims, 3 Drawing Sheets

Figure 1A:
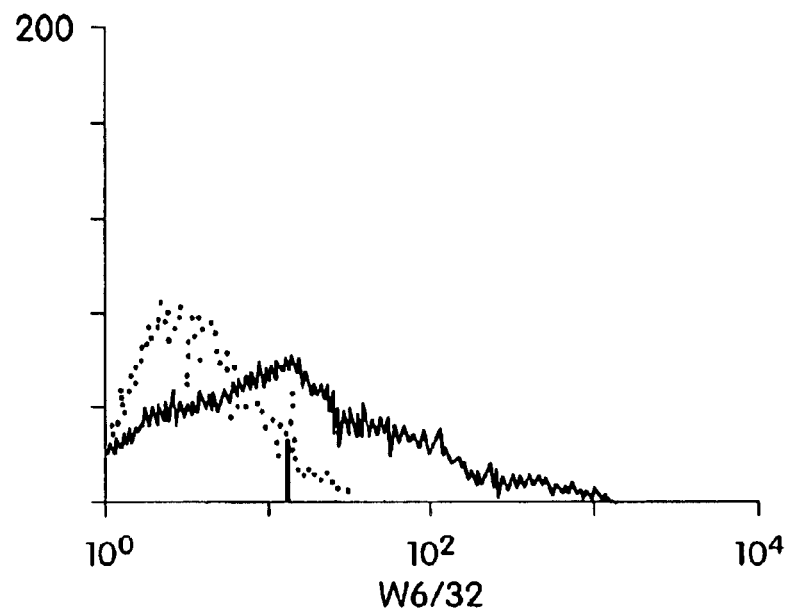

Fig. 2A
Fig. 2C
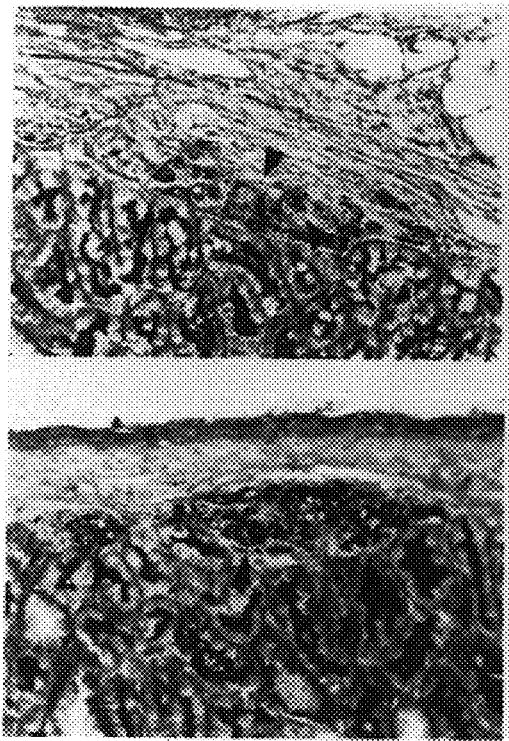
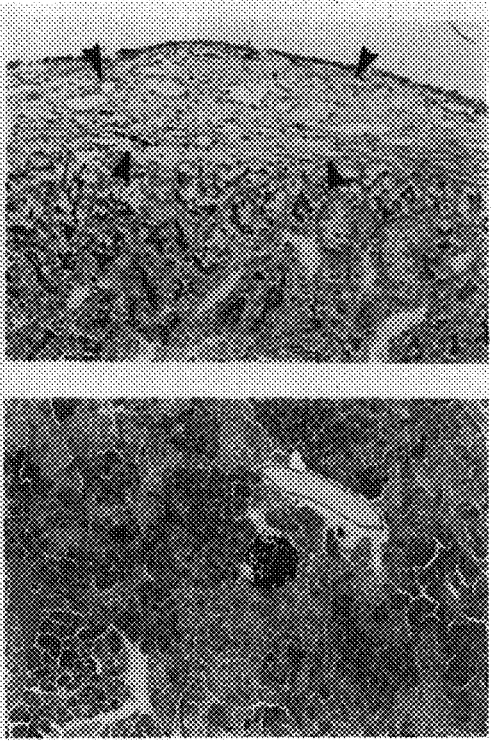
Fig. 2B
Fig. 2D

METHODS FOR INHIBITING REJECTION OF TRANSPLANTED TISSUE

This is a continuation of application Ser. No. 08/112,709, filed on Aug. 26, 1993, now U.S. Pat. No. 5,783,216 which is a divisional of application Ser. No. 07/671,517 filed Mar. 19, 1991, now U.S. Pat. No. 5,283,058 which is a continuation-in-part of application Ser. No. 07/575,150 filed Aug. 30, 1990, now abandoned.

BACKGROUND OF THE INVENTION

This application is a continuation-in-part of Faustman U.S. Ser. No. 07/575,150, filed Aug. 30, 1990. This invention relates to transplantation of tissues, e.g., islet cells, muscle cells, and whole organs, into hosts in need of such tissues, e.g., patients who have or are at risk of developing diabetes mellitus, have muscular dystrophy, or are in need of an organ transplant.

Diabetes mellitus is a prevalent degenerative disease, characterized by insulin deficiency, which prevents normal regulation of blood glucose levels, and which leads to hypergylycemia and ketoacidosis.

Insulin, a peptide hormone, promotes glucose utilization, protein synthesis, formation and storage of neutral lipids, and the growth of some cell types. Insulin is produced by the $\beta$ cells within the islets of Langerhans of the pancreas. Early-onset diabetes (10–20% of cases) is caused by an auto-immune reaction that causes complete destruction of $\beta$ cells. Adult-onset diabetes has a number of causes, but in most cases the $\beta$ islet cells are defective in secretion of insulin.

Insulin injection therapy, usually with porcine or bovine insulin, prevents severe hyperglycemia and ketoacidosis, but fails to completely normalize blood glucose levels. While injection therapy has been quite successful, it fails to prevent the premature vascular deterioration that is now the leading cause of morbidity among diabetics. Diabetes-related vascular deterioration, which includes both microvascular degeneration and acceleration of atherosclerosis, can eventually cause renal failure, retinal deterioration, angina pectoris, myocardial infarction, peripheral neuropathy, and arteriosclerosis.

Recently, cloning of the human insulin-encoding gene has allowed large scale production of human insulin, which has begun to replace bovine insulin and procine insulin as the treatment of choice. Use of human insulin has eliminated some of the problems associated with other forms of insulin, including antibody-mediated insulin resistance and allergic reactions resulting from the slightly different structures of non-human insulins. Despite these advantages, treatment with human insulin does not prevent vascular deterioration.

Insulin delivery pumps have been developed which administer varying doses of insulin based on activity, diet, time of day, and other pre-programmed factors. While such devices improve blood sugar control, they also do not prevent vascular deterioration.

Surgical transplantation of part or all of the pancreas is thought to be potentially the best treatment for diabetes. Successful transplantation is difficult, however, because the pancreas is a fragile and complicated organ, and it is impossible for a human donor to give only a portion of it; the only practicable source is a deceased donor. Further, only a small portion of the pancreas, the $\beta$ cells of the islet of Langerhans, produce insulin; the remainder of the pancreas presents a potent target for transplant rejection. Transplantation of just the islets of Langerhans is a desirable goal, as they continue to secrete appropriate amounts of insulin in response to nutritional signals even when isolated from the rest of the pancreas.

A major problem associated with transplantation therapy as a treatment for diabetes is that current regimes require life-long administration of immunosuppressive drugs. These drugs can cause increased susceptibility to infection, renal failure, hypertension, and tumor growth.

Despite these serious complications, islet transplantation has been successfully performed in experimental animals. Successful transplantation in rodents has been shown to restore normal blood glucose regulation and prevent further vascular deterioration. The broader application of allografts and xenografts (inter-species grafts) as a therapy for diabetes depends on preventing transplant rejection. It has long been known that culturing islets prior to transplantation decreases immunogenicity and increases transplant survival (Lacy et al (1979) Science 204_312; Lafferty et al. (1975) Science 188:259). It is thought that long term culturing removes the Ia-bearing passenger lymphoid cells, which are a primary stimulus for cell-mediated immunity and graft rejection. Faustman et al. (J. Exp. Med. 151:1673, 1980) found that islet cells lack Ia antigenic determinants and express class I antigen on their surfaces. This allowed Faustman et al. (Proc. Natl. Acad. of Sci. USA 78:5156, 1981) to develop a regime that used donor-specific anti-Ia serum and complement to destroy Ia bearing lymphoid cells in islets, and allowed transplantation across a major histocompatibility barrier into non-immunosuppressed diabetic mice.

SUMMARY OF THE INVENTION

The invention features a method for inhibiting rejection by a recipient animal of a transplanted tissue. The method involves modifying, eliminating, or masking an antigen which, when present on the surface of a cell of the tissue, is capable of causing a T-lymphocyte-mediated response in the animal; modification, elimination, or masking of the antigen inhibits antigen-mediated interaction between the cell and a T-lymphocyte of the animal, without causing lysis of the cell.

Where cells of the tissue for transplantation (the "donor" tissue) bear on their surfaces HLA class I antigens (members of one of the classes of major histocompatibility complex antigens), these antigens cause cytotoxic T-cell activation in recipients, terminating in donor cell lysis after several sequential activation steps. The cascade is initiated by non-specific conjugate formation between the CD8 receptor on host cytotoxic T-cells and the HLA class I antigens on the donor cell. Conjugate formation is followed by T-cell-mediated lysis, resulting in donor cell death. This lytic process can result in rejection even in intra-species transplantation. According to the invention, this problem is addressed by masking, modifying, or eliminating of the HLA class I antigens on the donor cells, so that the CD8-HLA class I antigen interaction which initiates the lytic cascade cannot occur.

As will be explained in more detail below, any T-cell receptor-interactive antigens on the surfaces or donor cells can advantageously be modified, eliminated, or masked according to the invention. The invention thus permits not just intra-species transplantation of tissues and organs, but xenografts as well, opening up the possibility of "farming" of donor organs and tissues in non-human animals for transplantation into human patients.

Preferred masking agent are F(ab')$_2$ fragments of antibodies to donor cell antigens; these fragments, while being capable of forming immune complexes with the antigen and thus preventing antigen-T-cell interaction, do not, because they have had the Fc portion of the antibody removed, fix complement and bring about cell lysis. It has been found that, even though one might not expect such F(ab')$_2$ fragments to bind tightly enough to permanently mask antigenic sites on donor cells, long-term host acceptance of such treated tissues can be achieved.

As will be explained in greater detail below, rejection-inducing surface antigens on cells of donor tissues can, in addition to being masked, be modified, e.g., by "capping", or wholly or partially eliminated by genetic manipulation, either in transgenic animals used as a source of donor tissue, or in culture.

Other features and advantages of the invention will be apparent from the following description of the preferred embodiments thereof, and from the claims.

DESCRIPTION OF THE PREFERRED EMBODIMENTS

The drawings are first briefly described.

Drawings

FIG. 1 is a set of a graphs illustrating the expression of HLA-class I (W6/32), CD29 (4B4), CD54 (ICAM-1) and CD58 (LFA-3) on freshly isolated 99–97% pure whole human islets of Langerhans by indirect immunoflourescence and flow cytometry. A. Human islets were positive at 36% with W6/32 antibody (- - -). B. Human islets were negative for CD29 with 9% expression (- - -). C. Human islets in this clean islet preparation were virtually negative for ICAM-1 with 14% expression (- - -). B. Human islets were negative for LFA-3 expression with 10.2% of the cells positive. Background goat anti-mouse FITC expression was 9% (- - -) for this experiment. An open gate with exclusion of dead cells and debris was used for flow cytometry. As expected, islet preparations contaminated with large amounts of fibroblast overgrowth or endothelial cells (purity 60–75%) were positive for low levels of LFA-3 and ICAM.

FIG. 2 is a series of photographs showing histologic analysis of human islets transplanted under the kidney capsule of Balb/c recipients A. Photomicrograph of human islet xenograft 30 days after transplant with pre-transplant treatment with HLA class I F(ab')$_2$ fragments (W6/32). This aldehyde fuscin stain (X100) shows well-granulated islets under the kidney capsule. B. Photomicrograph of human islet xenograft 200 days after transplant with pretransplant treatment with HLA class I F(ab')$_2$ fragments (W6/32). This aldehyde fuscin stain (X100) shows well-granulated islets under the kidney capsule. C. A control Balb/c mouse was transplanted with untreated fresh human islets and then killed at day 30. This characteristic photomicrograph shows the absence of donor islets and the presence of subcapsular fibrosis demonstrating the former area where the islets were transplanted. D. Aldehyde fuscin stain of a mouse islet in the mouse pancreas demonstrating the characteristic purple granulation of healthy beta cells.

Donor Tissue Preparation

Before describing in detail specific examples of the invention, there is a brief discussion of some parameters of the invention.

Donor Tissues

In addition to permitting transplantation of islet cells, the invention can facilitate transplantation of any other tissue or organ, e.g., kidney, heart, liver, lung, brain, and muscle tissue.

Antigens to be Masked, Modified, or Eliminated

The invention can be used to mask, modify, or eliminate any host T-cell-interactive antigen on any of the cells of the donor tissue. In addition to HLA class I antigens, which are found on all parenchymal cells, including islet cells, other important donor cell antigens known to interact with host T-cells to bring about rejection are LFA-3 and ICAM-1; these react, respectively, with the host T-cell receptors CD2 and LFA-1. Both LFA-3 and ICAM-1 are found on endothelial cells which make up blood vessels in transplanted organs such as kidney and heart. Masking, altering, or eliminating these antigens will facilitate transplantation of any vascularized implant, by preventing recognition of those antigens by CD2+ and LFA-1+ host T-lympohcytes. Further, masking, altering, or eliminating a particular donor cell antigen may render more than one donor cell-type less susceptible to rejection. For example, not only do parenchymal cells such as islet cells bear HLA class I antigens, but passenger lymphocytes bear such antigens as well, and if such lymphocytes are present in a donor tissue preparation, removal of an HLA class I antigen or treatment of the tissue preparation with an HLA class l antigen masking agent will render those lymphocytes less antigenic.

The antigens HLA class 1, LFA-3, and ICAM-1 are well-characterized, and antibodies to these antigens are publicly available, and can be made by standard technique. For example, anti-ICAM-1 can be obtained from AMAC, Inc., Maine; hybridoma cells producing anti-LFA-3 can be obtained from the American Type Culture Collection, Rockville, Md.

Where the donor tissue to be transplanted bears more than one T-cell-interactive antigen, two or more treatments, e.g., two or more masking agents, may be used together. Alternatively, a polyclonal antisera generated against the donor tissue may be used to mask multiple cell surface antigens of the donor tissue.

Non-Lytic Masking Agents

Generally, the invention can employ three categories of masking agents: (1) antibodies or fragments or derivatives thereof; (2) soluble fragments or analogs of antigen-specific host T-cell receptors; and (3) synthetic organic molecules which mimic the antigen binding properties of T-cell receptors.

Antibodies, the currently most preferred masking agents, can be used either as one or more antigen-specific preparations, or as whole donor organ or tissue antisera preparations. In either case, it is necessary that the preparations be unable to fix complement and bring about donor cell lysis. Complement fixation can be prevented by deflection of the Fc portion of the antibody, by using an antibody isotype which is not capable of fixing complement, or, less preferably, by using a complement fixing antibody in conjunction with a drug which inhibits complement fixation.

Individual antigen-specific antibodies can be made by standard procedure, including immunization of an animal, e.g., a mouse, with the antigen to be masked, followed by hybridoma preparation and antibody screening according to standard methods. Alternatively, whole donor antisera can also be used. For example, where the donor tissue is derived from a pig, whole pig antisera are produced by immunization of a mouse with pig donor tissue or pig lymphocytes, followed by screening for antibodies which block human T-lymphocyte adhesion to pig donor cells.

As an alternative to antibodies or antibody fragments, masking can be effected by use of soluble host T-cell receptor which competitively inhibits binding of those T-cells to donor tissue cell antigens, by occupying the antigenic site on the tissue which would otherwise interact with the host T-cells. T-cell molecules or proteins, e.g., CD8, CD2, and LFA-1, are well characterized proteins generally having an extracellular domain, a transmembrane region, and a cytoplasmic domain which bend to target cell ligands. Soluble T-cell receptor protein fragments can be made by standard recombinant DNA procedures, in which the DNA encoding the transmembrane and cytoplasmic domains is deleted, and the extracellular domain DNA is expressed in recombinant cells to produce soluble recombinant protein.

Capping

Capping is a term referring to the use of antibodies to cause aggregation and inactivation of surface antigens. First, the tissue is contacted with an antibody specific for the antigen, so that antigen-antibody immune complexes are formed. The next step is contacting the tissue with a second antibody capable of forming immune complexes with the first antibody, so that the first antibody is aggregated to form a cap at a single location on the cell surface. The technique is well known, and has been described, e.g., in Taylor et al. (1971), Nat. New Biol. 233:225–227; and Santiso et al. (1986), Blood, 67:343–349. In the case of cells, e.g., islet cells, bearing HLA class I antigens, the first step is to incubate the cells with antibody (e.g., W6/32 antibody, described below) to HLA class I, and then to incubate with antibody to the donor species, e.g., goat anti-mouse antibody, to bring about aggregation.

Transgenic Animals with Decreased HLA Class I Expression

As an alternative or an adjunct to masking surface antigens on cells of donor tissues prior to transplantation, such tissues can be grown in transgenic animals which have been genetically altered so that surface antigen expression is diminished. Such transgenic animals can be made by standard transgenic techniques, employing genes which delete or inactive the gene encoding the target antigen, or delete or inactive a gene necessary for its expression on the cell surface, by homologous recombination.

For example, in the case of HLA class I expression, homologous recombination can be used either to delete or inactivate the HLA class I molecule itself, or to inactivate or delete a companion molecule necessary for its surface expression. The HLA class I molecule is a protein composed of a 32 kd and a 45 Kd chain, associated with another protein, $\beta$-2 microglobulin. The highly conserved $\beta$-2 microglobulin protein is believed to function as a carrier molecule which facilities class I assembly in plasma membranes.

Inhibition of class I expression on the surfaces of cells, e.g., islet cells, can thus be achieved either by deletion or inactivation of one of the HLA class I chains, or by deletion or inactivation of the carrier $\beta$-2 microglobulin molecule. Disruption of $\beta$-2 microglobulin expression in transgenic animals resulting in decreased HLA class I expression has been carried out by several groups (Koller and Smithies (1989), PNAS USA 86:8932–8935; zijlstra et al. (1990) Nature, 344:742–746; Doetschman et al. (1987) Nature, 51:503–512).

In Vitro Methods to Decrease HLA Class I Expression

A number of oncogenic viruses have been demonstrated to decrease HLA class I expression in infected cells; Travers et. (1980) Int'l. Symp. on Aging in Cancer, 175–180; Rees et al. (1988) Br. J. Cancer, 57:374–377. In addition, it has been demonstrated that this effect on HLA class I expression can be achieved using fragments of viral genomes, in addition to intact virus. Transfection of cultured kidney cells with fragments of adenovirus causes elimination of surface HLA class I antigenic expression; Whoshi et al. (1988) J. Exp. Med. 168:2153–2164. For purposes of decreasing HLA class I expression on the surfaces of donor cells, e.g., islet cells, viral fragments, which are non-infectious, are preferable to whole viruses, which could cause complications. Other viruses and viral fragments could be used to decrease expression of other surface antigens on other types of donor cells, as well as decreasing expression of HLA class I expression on parenchymal cells such as islet cells.

Local Blockage of Recipient T-Cell Receptors With Secreted Donor Antigens

The transplantation inhibition strategies discussed above all involve altering the donor tissue such that surface antigens on donor tissue cells which are recognized as foreign by receptors on recipient T-cells are eliminated, modified, or masked. An alternative strategy is to modify the donor tissue in a different way, which brings about blockage of the host T-cell receptors by antigen secreted by donor cells. For example, in the case of donor tissue containing parenchymal cells bearing surface HLA class I antigen, rather than masking the antigen, those cells can be transfected with DNA encoding soluble antigen, which is secreted and which competitively binds to the CD8 receptor on the T-lymphocytes of the recipient which would otherwise bind to membrane-bound HLA class I antigen on the donor tissue cells. The techniques for carrying out this procedure will be analogous to methods used by other workers to bring about secretion of a recombinant protein in concert with insulin secretion; Lo et al. (1988) Cell, 53:159–168; Adams et al. (1987) Nature, 325:223–228. Adams et al. achieved SV40 T antigen synthesis in islet cells in concert with insulin production. HLA class T antigen expression and secretion could be coupled to insulin production and secretion by placing the gene for one or both subunits of HLA class I antigen under the control of insulin gene regulatory sequences. Insulin secretion thus will result in simultaneous expression and secretion of HLM class I antigen. This strategy has the advantage of causing secretion of HLA class I antigen only from islet cells, in tissue which may contain other cell types as well; none of the other cells present produce and secrete insulin. In addition, this approach confines the soluble HLA class I antigen to the localized region where it is needed, i.e., in the area immediately surrounding the transplanted islet cells.

The following specific examples are for illustration purposes only, and are not intended to limit the scope of the invention.

EXAMPLE 1

This example involves xenogeneic transplantation of HLA class I positive human islet cells into nonimmunosuppressed Balb/c mouse recipients. Freshly isolated human islets were pretreated prior to transplantation with whole monoclonal antibody or $F(ab')_2$ monoclonal antibody fragments to conceal ("mask") donor antigens. $F(ab')_2$ fragments lack the Fc antibody region, thus circumventing complement-mediated killing after antigen binding. Intact immunoglobulin was used as a control. Human islets were treated with relevant HLA class I monoclonal antibody (W6/32) (American Tissue Culture Society) (Barnstable et al. (1978) Cell, 14:9–20) or irrelevant CD29 monoclonal antibody (Coulter Corporation, Hialeah, Fla.). Clean human islet preparations, free of contaminating endothelial and fibroblast overgrowth, are negative for ICAM-1 expression, negative for CD29 expression, have low LFA-3 expression, and are positive for HLA class I antigens (FIG. 1). Therefore, islets, unlike other cytotoxic T-lymphocyte targets, lack the prominent expression of the two important adhesion epitopes LFA-3 and ICAM-1, and there is little need to protect these adhesion epitopes from T-cell binding.

F(ab')$_2$ fragments were generated using an immobilized pepsin. Purified antibody added at 20 mg/ml in pH 4.7 digestion buffer was digested for 4.5 hours for CD29 antibody and 4.0 hours for W6/32 antibody (HLA class I) at 37° C. in a shaker water bath (Pierce Chemical, Rockford Ill.). The crude digest was removed from the pepsin and immediately neutralized with pH 7.0 binding buffer. This antibody mixture was applied to an immobilized Protein A column and the eluate collected for the F(ab')$_2$ fragments. Dialysis against PBS for 24 hours using 50,000 M.W. cutoff tubing was then performed to rid the digest of contaminating Fc fragments. CHAPPS was added to the dialysis bag at a concentration of 10 mM. The completeness of the digest and purification of the F(ab')$_2$ digests were monitored by silver staining of 15% SDS gels. Final purification of the fragments was achieved by HPLC using a Superose 12 column (Pharmacia, Upsala, Sweden).

F(ab')$_2$ fragments or whole antibodies were incubated with human islets at a concentration of 1 μg of antibody for approximately 1×10$^6$ islet cells for 30 minutes at room temperature. After incubation, the treated or untreated islets were washed once in Hanks buffer containing 2% FCS and then immediately transplanted under the kidney capsule by syringe injection. The human islets used were transplanted within 4 days after isolation. Ten to twelve week old Balb/c female nice (The Jackson Laboratories, Bar Harbor, Me.) were transplanted with 2200–4500 human islets. At 30 or 200 days post transplantation the mice were sacrificed by cervical dislocation and the kidney containing the transplanted tissue was surgically removed and immediately fixed in Bouin's solution.

Figure 1B:
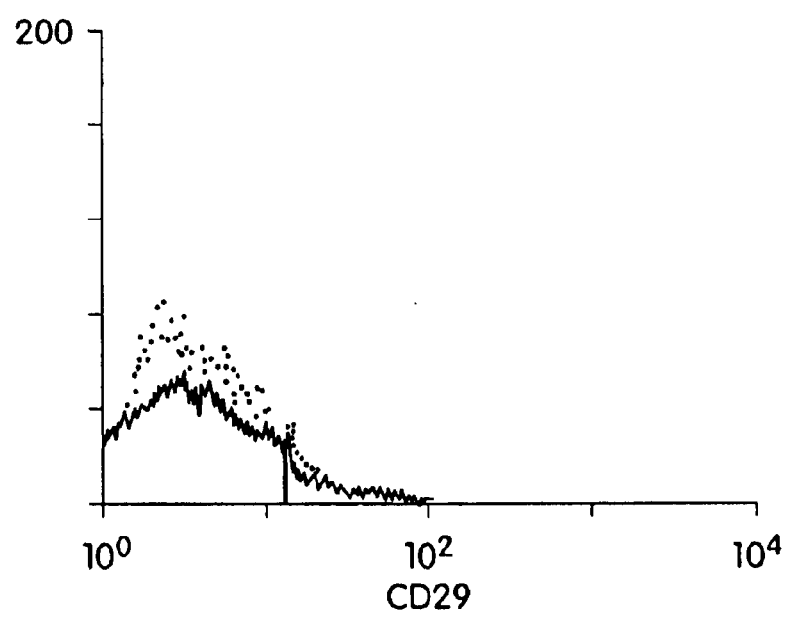

The results of the transplantation studies are summarized in Table I. W6/32 F(ab')$_2$ pretreatment of donor xenogeneic islets (HLA class I) resulted in complete islet xenograft survival in all 5 recipients evaluated at 30 days after transplantation (Group 1) as well as all 5 recipients evaluated at 200 days after transplantation (Group 2). The histology in all 10 mice revealed well-granulated islets under the kidney capsules (FIG. 1A, 1B). Untreated human islets were promptly rejected by 7 days in this mouse model; histology in these mice showed massive lymphocytic infiltrates under the kidney capsules and no granulated islets cells. The HLA class I F(ab')$_2$ treated islet grafts (W6/32) were virtually free of adjacent lymphocyte deposits even at 200 days following transplantation (FIG. 1B). Lymphocytic accumulations are a known characteristic of xenograft transplants prolonged with culture.

Figure 1C:
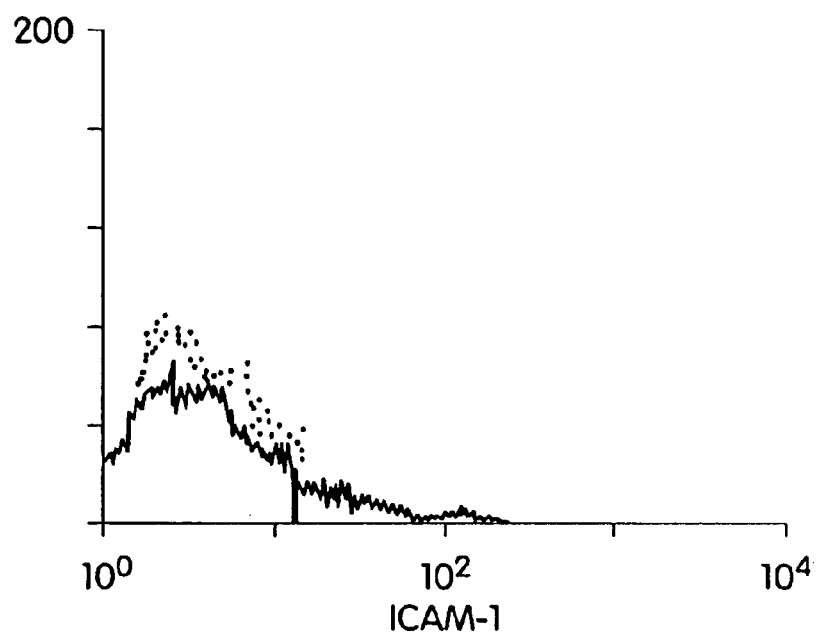
Figure 1D:
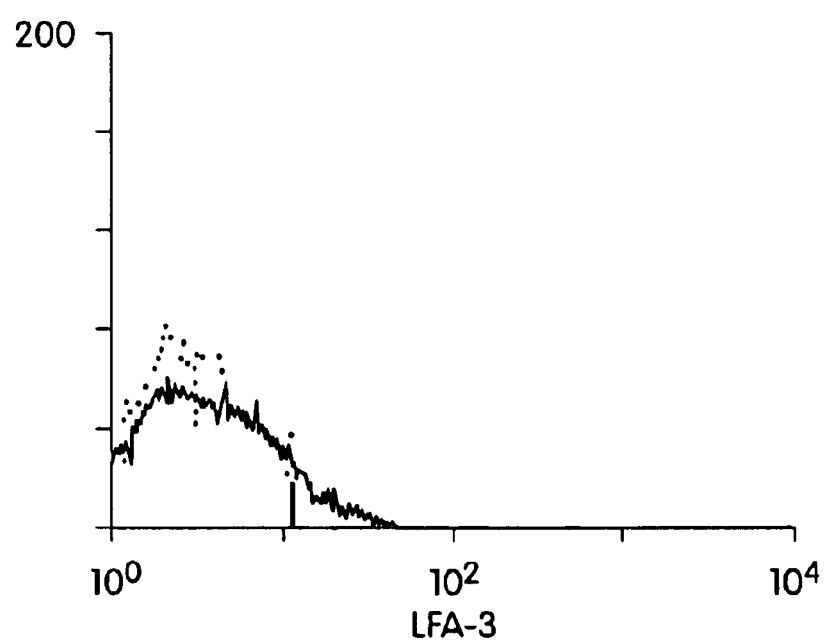

Balb/c recipients receiving islet grafts pretreated with whole HLA class I W6/32 antibody demonstrated no surviving islet tissue at 30 or 200 days after transplantation (Group 3, 4) (Table 1), indicating probable complement fixation and lysis by the whole, uncut antibody. Histology performed on these transplants revealed subcapsular kidney fibrosis at the transplantation site (FIG. 1C). The coating of donor islets with irrelevant F(ab')$_2$ fragments directed at CD29 resulted in islet graft rejection by day 30 as well as day 200 (Group 5, 6). Intact, CD29 antibody also failed to prolong islet xenograft survival (Group 7, 8). The pretreatment of donor human islets with specific HLA class I F(ab')$_2$ antibody fragments (W$_{6/32}$) and with irrelevant CD29 F(ab')$_2$ antibody fragments (CD29) resulted in graft survival in all five recipients at day 30 (Group 9) and all five recipients at day 200 (Group 10) as observed for HLA class I F(ab')$_2$ fragments alone. As expected, untreated human islets were absent at both the 30 day and 200 day evaluation time points (Group 11, 12). Only subcapsular fibrosis was present under the kidney capsule at day 30 (FIG. 1C) and day 200 in these recipients.

The function of transplanted human islets was monitored by evaluating human insulin C' peptide levels at 30 and 200 days post transplantation (Table 2). All 20 recipients receiving W6/32 F(ab')$_2$ coated human islets or W6/32 F(ab')$_2$ and CD29 F(ab')$_2$ coated islets at day 30 had detectable human C' peptide levels markedly above background levels (Group 1, 2, 9, 10) (p=0.002). Human C' peptide levels were similarly detected at 200 days in all ten recipients receiving W6/32 F(ab')$_2$ antibody coated islets (Groups 2, 10) (p=0.003). In contrast, all individuals in the control transplant groups had human C' peptide levels similar to background levels (Group 3, 4, 5, 6, 7, 8, 11, 12) (p=0.98).

EXAMPLE 2

This example involves the xenogenenic transplantation of rat insulinoma tumor cells (RIN) into nonimmunosupressed Balb/c mouse recipients to investigate the possibility of graft specific tolerance with growth of a transplanted tissue pretreated with polyclonal F(ab')$_2$.

RIN tumor cells are an established rat insuloma tumor cell line (Meflasson et al., 1983 J. Biol. Chem. 258:2094–2097). Polyclonal mouse anti-RIN serum was produced and F(ab')$_2$ antibody fragments were generated as described above in Example 1. As expected, xenogeneic RIN cells (approx. 5,000 cells per recipient) transplanted under the kidney capsule of nonimmunosuppressed BALB/c mice were uniformly rejected when evaluated by histology with aldehyde fuscin staining (n=4) (Table 3). In addition, pretreatment of RIN cells with intact polyclonal mouse anti-RIN antibody, without removal of the complement-fixing Fc region, prior to transplantation also failed to protect grafts from recipient mediated rejection (n=4). In contrast, pretreatment of RIN cells with F(ab')$_2$ fragments of mouse anti-RIN polyclonal antibodies allowed RIN cell survival at one, two, three, and four months after transplantation. Even though each BALB/c recipient received an equal number of cells at the time of transplantation, serial sections through the transplant site under the kidney capsules at different monthly intervals after transplantation revealed a noticeable increase in the mass of tumor tissue, suggesting tumor growth. In addition, the successfully transplanted RIN cells demonstrated mitosis on hematoxylin and eosin staining, confirming cell division and presumably the new expression of unmasked foreign antigens. The continued survival and expansion of a xenogeneic tumor cell line suggests the possible presence of graft induced tolerance in the recipients. Further proof of a state of graft tolerance was obtained by transplanting F(ab')$_2$ coated RIN cells unilaterally into the right kidney of non-immunosuppressed mice for 30 days prior to a secondary transplant of untreated RIN cells into the left kidney. At day 60 the four mice transplanted in this manner were sacrificed. The four untreated secondary transplants of insulinoma cells also demonstrated survival, confirming the suspected development of a systemic tolerant state sufficient for fresh tumor cell survival.

EXAMPLE 3

The effectiveness of F(ab')$_2$ HLA class I antibody coating in preventing rejection of non-tumorgeneic human liver cells in xenogeneic transplants was also investigated. Approximately 5,000 fresh human liver cells from the parenchymal tissue of the liver were injected into the subscapular space of the kidney capsules of nonimmunosuppressed mouse recipients. Histological examination using PAS staining of the subscapular sites indicated that all 5 transplant recipients of F(ab')$_2$-treated liver cells demonstrated easily located viable liver cells at the subscapular renal site 30 days after transplantation. As expected, untreated human liver cells were uniformly rejected in all five mice by day 30 after transplantation.

It is clear from the results of Examples 1 and 3 that the simple interruption of recipient T cell recognition by masking of foreign HLA class I determinants allows prolonged xenograft survival up to 200 days. This new strategy eliminates recipient treatment, thus preserving the immune response of the host so that it remains available for recognition of relevant pathogens.

The prolonged duration of recipient unresponsiveness to a viable tissue which eventually might lose the masking antibody or exhibit the ability to resynthesize new uncoated HLA class I determinants suggests that graft specific tolerance may stabilize these transplants. This is substantiated by the lack of large foci of lymphocyte infiltrates in my successful xenografts. This is consistent with may assumption that donor pretreatment of the graft with HLA class I antibody fragments coats class I antigens on transient donor dendritic cells as well as class I antigen on the parenchymal islet cells. With the passage of time post-transplantation, these antigen presenting cells which are potent graft rejection initiators may die off, as occurs with extended culture, thus gradually exposing the recipient to low levels of HLA class I antigens on non-antigen presenting cells.

OTHER EMBODIMENTS

Other embodiments are within the following claims. For example, the procedures described above for treatment of islet cells and liver cells can be used to treat muscle cells for transplantation into patients with muscular dystrophy, as follows; muscle cells, like islet cells, bear rejection-stimulating HLA class I antigens, and also express class II antigens. Human donor muscle cells will be obtained by biopsy of living related donors or brain dead donors using a 14–16 gauge cutting trochar into a 1–2 inch skin incision. The fresh muscle plug will then be lightly digested into a single cell suspension using collagenase, trypsin and dispase at 37° C. Floating debris will be removed with a pipet and media washes and the viable cell pellet counted after centrifugation at 1000 rpm×10 minutes. This cell count will then be used to calculate the amount of HLA class II antibody fragments to add; treatment will be as described above for islet cells. Similarly, the invention will permit transplantation of cells, from a healthy individual or which have been genetically engineered, into recipients who have a deficiency for a particular cellular component. For example, individuals with hemophilia might be recipients of Factor VIII-producing liver cells from normal donors, or of cells which have been genetically engineered to secrete Factor VIII.

Another embodiment of the invention would be the transplantation into patients of whole organs (e.g. heart, lung, liver, kidney). A preferred organ masking pre-treatment procedure would involve perfusion of the donor organ with F(ab')$_2$ fragments of monoclonal antigen-specific antibodies or with polyclonal antisera generated against the organ tissue; perfusion is carried out using conventional techniques for perfusing donor organs with other fluids.

What is claimed is:

1. A transplantable composition for use in humans comprising isolated cells or isloated tissue of a type normally bearing an HLA class I surface antigen that causes an immune response against the cell or tissue in a human recipient, wherein the antigen is masked to decrease said immune response, such that upon introduction of the composition into a human, lysis of said cell or tissue is prevented; wherein said class I antigen is masked by contacting said cell or tissue with an antibody lacking the Fc portion, which does not fix complement and, which is capable of forming a complex with said class I antigen on said cell or tissue.

2. The composition of claim 1, wherein the antibody lacking the Fc portion is a F(ab')$_2$ fragment of an antibody.

3. The composition of claim 1, wherein the antibody lacking the Fc portion is obtained from polyclonal antisera raised against the antigen.

4. The composition of claim 1, wherein the cell or tissue has at least two different antigens which are masked with at least two different antibodies lacking the Fc portion.

5. The composition of claim 1, which comprises a neuronal cell.

6. The composition of claim 1, wherein the cell is a non-lymphocytic cell.

7. The composition of claim 1, wherein the tissue comprises non-lymphocytic cells.

* * * * *

UNITED STATES PATENT AND TRADEMARK OFFICE
CERTIFICATE OF CORRECTION

PATENT NO. : 6,844,011 B1
DATED : January 18, 2005
INVENTOR(S) : Denise Faustman It is certified that error appears in the above-identified patent and that said Letters Patent is hereby corrected as shown below:

Column 10,
Line 24, replace "isloated" with -- isolated --.

Signed and Sealed this

Fifth Day of April, 2005

JON W. DUDAS
*Director of the United States Patent and Trademark Office*